United States Patent
Bornefeld et al.

(10) Patent No.: US 10,067,039 B2
(45) Date of Patent: Sep. 4, 2018

(54) METHOD AND APPARATUS FOR PRODUCING A PELLET

(71) Applicant: THYSSENKRUPP INDUSTRIAL SOLUTIONS AG, Essen (DE)

(72) Inventors: Marc Bornefeld, Bielefeld (DE); Reinhard Teutenberg, Unna (DE); Jürgen Schneberger, Ennigerloh (DE)

(73) Assignee: THYSSENKRUPP INDUSTRIAL SOLUTIONS AG, Essen (DE)

( * ) Notice: Subject to any disclaimer, the term of this patent is extended or adjusted under 35 U.S.C. 154(b) by 150 days.

(21) Appl. No.: 14/902,786

(22) PCT Filed: Jun. 27, 2014

(86) PCT No.: PCT/EP2014/001766
§ 371 (c)(1),
(2) Date: Jan. 4, 2016

(87) PCT Pub. No.: WO2015/000571
PCT Pub. Date: Jan. 8, 2015

(65) Prior Publication Data
US 2016/0161377 A1    Jun. 9, 2016

(30) Foreign Application Priority Data
Jul. 3, 2013  (DE) .................. 10 2013 106 998

(51) Int. Cl.
C03B 19/10 (2006.01)
G01N 1/28 (2006.01)
G01N 1/44 (2006.01)

(52) U.S. Cl.
CPC .......... G01N 1/286 (2013.01); C03B 19/1085 (2013.01); G01N 1/44 (2013.01); *G01N 2001/2866* (2013.01)

(58) Field of Classification Search
None
See application file for complete search history.

(56) References Cited

U.S. PATENT DOCUMENTS

| | | |
|---|---|---|
| 3,890,089 A | 6/1975 | Matocha |
| 4,013,784 A | 3/1977 | Speiser |
| 4,131,478 A * | 12/1978 | Davis ..................... C03C 8/245 501/15 |
| 4,839,516 A | 6/1989 | Freeman |
| 5,257,302 A | 10/1993 | Narukawa |
| 6,242,392 B1 | 6/2001 | Hoffmann et al. |
| 2011/0081396 A1 * | 4/2011 | Denry .................... A61L 27/10 424/423 |

FOREIGN PATENT DOCUMENTS

| | | |
|---|---|---|
| CN | 1034270 A | 7/1989 |
| CN | 101823013 A | 9/2010 |
| DE | 2624941 A1 | 12/1976 |
| DE | 2360796 B2 | 6/1977 |
| DE | 102004050720 A1 | 4/2006 |
| EP | 1052500 A2 | 11/2000 |
| FR | 2248479 A1 | 5/1975 |
| GB | 1524126 A | 9/1978 |
| JP | S5931439 A | 2/1984 |
| WO | 89/04475 A1 | 5/1989 |

OTHER PUBLICATIONS

German language International Search Report for International patent application No. PCT/EP2014/001766; dated Sep. 18, 2014.
English translation of International Search Report for International patent application No. PCT/EP2014/001766; dated Sep. 18, 2014.
English translation of the abstract for JPS5931439 (A).
English translation of the abstract for DE102004050720 (A1).

* cited by examiner

*Primary Examiner* — Cynthia Szewczyk
(74) *Attorney, Agent, or Firm* — thyssenkrupp North America, Inc.

(57) ABSTRACT

Disclosed is a method and an apparatus for producing a pellet preferably intended for subsequent chemical analysis, wherein a material stream is melted, the molten material is shapelessly cooled and ground and at least some of the ground material stream is pressed into a pressed pellet.

11 Claims, No Drawings

METHOD AND APPARATUS FOR PRODUCING A PELLET

CROSS REFERENCE TO RELATED APPLICATIONS

This application is a U.S. National Stage Entry of International Patent Application Serial Number PCT/EP2014/001766, filed Jun. 27, 2014, which claims priority to German patent application no. DE 102013106998.3 filed Jul. 3, 2013, the entire contents of both of which are incorporated herein by reference.

FIELD

The invention relates to a process and an apparatus for producing a pellet preferably intended for subsequent analysis to identify substances.

BACKGROUND

Producing pellets in the form of pressed pellets by grinding the pellet material and further processing said material by employment of pressure and/or binding agent to afford the pellet is prior art. A process of this type requires that, prior to grinding, the pellet material already has a consistency suitable for the finished pellet.

Producing pellets from a melt is also prior art. This comprises melting the pellet material, pouring the melt into a pellet mould and cooling it therein. However, such cooling with simultaneous shaping entails complexity both in terms of process engineering and in terms of apparatus. For instance, cooling of a fused pellet must be performed under precisely controlled conditions since excessively rapid cooling results in fracture of the pellet while excessively slow cooling leads to crystallization of the melt so that the pellet likewise loses its strength.

Accordingly there is a need for a method and an apparatus for producing a pellet preferably intended for subsequent chemical analysis, wherein said method and apparatus are substantially simpler, both in terms of process engineering and in terms of apparatus complexity, than previously known processes and apparatuses.

DETAILED DESCRIPTION

While in the prior art processes for producing a pellet from a molten material stream the melt is poured into a mold in a defined fashion and cools down therein to afford a pellet, the process according to the invention comprises shapelessly cooling the molten material stream. Here, the glassy material solidifies to a random shape and is subsequently ground and pressed into a pressed pellet. The rate of this shapeless cooling of the molten material stream is not critical, thus substantially simplifying the entire process.

A glassy material/a glassy structure is to be understood as meaning in particular an amorphous material which after cooling from the melt does not exhibit a crystalline structure. Such a glassy material is obtained, for example, by rapid cooling of the melt to prevent crystallization of the material. The crystallographic properties of the material stream are preferably retained after the cooling of the material stream so that the ground material stream downstream of grinding step c), and the pressed pellet downstream of step d) comprising pressing at least some of the ground material stream into a pressed pellet, have a glassy structure. Neither the grinding of the cooled material stream nor the pressing of the material stream downstream of the grinding alter the crystallographic properties of the material stream and the glassy structure is retained.

The glassy, amorphous structure of the pressed pellet makes subsequent analysis, for example of the composition of the pellet, possible. Moreover, the preceding grinding and pressing makes such a pellet having a glassy structure significantly more robust than a glassy pellet cooled from the melt.

This affords, without shaping the melt but rather from the shapelessly cooled material stream, a pressed pellet which surprisingly yields the same analytical results as are obtained with a conventional fused pellet of the prior art type particularized at the outset. The step of shaping the pellet from the melt, which was hitherto regarded as essential in the art, was found not to be necessary in the experiments underlying the present invention. The inventive omission of a complex step of shaping with simultaneous cooling substantially simplifies pellet production both in terms of process engineering and in terms of apparatus.

The process according to the invention thus combines the techniques of producing a melt, of cooling a melt without complex shaping, and of grinding, with the techniques of pressing a pressed pellet. The novel process allows for substantially simpler handling of the pressed pellet compared to conventional fused pellets in automated environments. A pressed pellet produced in accordance with the invention is moreover markedly more robust than a fused pellet produced by the prior art process. The pressed pellet according to the invention is highly impervious to handling, in particular by a robot, and does not shatter when correctly prepared.

A further advantage of the process according to the invention is the omission of the additional permanent molds (casting molds) made of platinum that are required for the manufacture of the prior art fused pellets.

According to one advantageous embodiment of the process according to the invention, the shapelessly cooled material stream is ground to a grain size of <2 mm, preferably <1 mm.

The grinding may also completely or partly be effected simultaneously with the cooling of the molten material stream.

The melt may be homogenized during and/or after the melting operation, preferably by stirring, shaking and/or agitating.

Cooling of the molten material stream may be achieved via a cooling gas and/or a cooling liquid, preferably by means of a metallic surface, for instance a cooled or uncooled metal plate.

The grinding advantageously comprises at least a pre-grinding and a main grinding, wherein the pregrinding has a duration of more than 30 seconds, preferably more than 150 seconds, in particular more than 280 seconds and wherein the main grinding has a duration of more than 25 seconds and less than 200 seconds. One or more grinding aids may be employed in the pregrinding and/or in the main grinding.

The grinding advantageously employs a superfine mill operating at between 650 and 1850 rpm.

According to a further embodiment of the invention, the cooling assembly may comprise rollers or balls and may also serve to comminute the unshaped molten material stream.

The cooling assembly may also comprise means that generate a gas and/or liquid curtain through which the unshaped molten material stream passes.

The superfine mill may advantageously comprise a vibratory disk mill, a ball mill, a roller mill or a combination of these mill types.

The press may be a ram press.

The pressed pellet produced according to the inventive process is generally intended for subsequent chemical analysis. To this end, said pellet is sent to a suitable analytical instrument, preferably an XRF instrument.

The chemical analysis of pressed pellets by x-ray fluorescence analysis (XRF) may in principle be performed on any solid. However, organic substances are rarely considered since they would generally be incinerated at the high temperatures during the melting.

It is generally a mixture of sample material and flux that is melted. The mass ratio between the flux and the sample material is constant for all samples and is preferably 6:1.

The chemical composition is not changed by the melting operation and cooling.

The flux renders the melting point independent of the sample material. The melting point of the mixture is generally about 850° C.-1500° C., in particular 1050° C.-1100° C.

Cooling to room temperature generally takes 4-8 minutes.

To further elucidate the invention the five steps for producing a pressed pellet via a melt are described herein below.

1. Metering of materials:

The sample material and a flux (lithium tetraborate, Spectromelt) are metered via a metering apparatus (for example a vibrating chute). The metered amount should be 6-15 g, the ratio between flux and sample material being kept constant for all samples. The mixture is poured into a crucible, preferably made of platinum, graphite, corundum or another suitable ceramics material.

The mixture may be preground prior to melting to achieve improved commixing of sample material and flux.

2. Melting:

The metered mixture is melted over a gas flame in an oven (for instance an induction oven or muffle oven). To homogenize the melt, a suitable apparatus, in particular a stirring, shaking, or agitating device, may be employed.

3. Cooling:

The melt is rapidly cooled, for instance by one of the following methods:

pouring the melt onto a cooled metal plate to which an apparatus is connected which detaches the cooled melt from the plate via a mechanical impulse and subsequently cleans said plate. Where necessary, an apparatus for comminuting fused lumps is provided below the metal plate.

pouring the melt into a small roller mill ("Mini Polycom"). The rotation of the rollers cools said rollers and the melt.

pouring the melt into a cooling liquid.

Where necessary, the relatively coarse particles of the cooled melt are crushed to attain a grain size of <5 mm.

4. Production of a pressed pellet:

The cooled melt is sent to a fine mill. Metered addition is not necessarily required. The grinding may comprise a pregrinding and a main grinding, or a single grinding step. The fine mill operates at between 650 and 1850 rpm.

When there is sufficient sample material a presample is defined which is ground in the mill prior to the actual sample and discarded. This avoids any potential contamination by preceding sample material.

Grinding may be performed in the presence of grinding aids.

5. Pressing of the ground material into a pressed pellet.

Steps 4 and 5 may be performed using either a combined grinding and pressing device or a fine mill and a pellet press. In the latter case, material is transported from the fine mill to the pellet press via a robot or a conveyor belt for example.

What is claimed is:

1. A method for producing a pellet to be analyzed, so as to identify the substances contained therein, the method comprising:
    melting a material to produce a molten material stream;
    shapelessly cooling the molten material stream to produce a glassy material;
    grinding the cooled glassy material; and
    pressing at least a portion of the ground glassy material to form a pressed pellet,
    wherein said grinding of the glassy material is at least partially performed at the same time as said cooling thereof.

2. The method of claim 1, wherein said grinding step comprises grinding the cooled glassy material down to a grain size of less than 2 mm wide.

3. The method of claim 1, further comprising homogenizing the melted material at least one of during or after said melting step, by at least one of a stirring, a shaking, and an agitating process.

4. The method of claim 1, wherein said cooling step comprises subjecting the molten material stream to a cooling liquid or contacting the molten material stream with at least one of a cooled or uncooled metallic surface.

5. The method of claim 1, wherein said grinding step comprises pregrinding the cooled glassy material for at least 30 seconds, and main grinding the preground glassy material for between 25 seconds and 200 seconds.

6. The method of claim 5, wherein at least one of said pregrinding step and said main grinding step utilize a grinding aid to assist in the performance of said respective grinding steps.

7. The method of claim 1, wherein said grinding step is performed by a superfine mill having grinding heads operating at between 650 rpm and 1850 rpm.

8. The method of claim 1, further comprising, after said grinding step, feeding the ground glassy material to a pressing device.

9. The method of claim 1, wherein said cooling step comprises subjecting the molten material stream to a cooling gas.

10. The method of claim 1, wherein said cooling step comprises contacting the molten material stream with at least one of a cooled and an uncooled metallic surface of a metal plate.

11. The method of claim 1, wherein the step of shapelessly cooling the molten material stream to obtain a glassy material comprises pouring the melt into a cooling assembly which comprises at least one of a plurality of rollers and a plurality of balls configured to comminute the unshaped molten material.

* * * * *